United States Patent
Uedaira et al.

(10) Patent No.: US 9,808,162 B2
(45) Date of Patent: Nov. 7, 2017

(54) PULSE WAVE SENSOR AND SEMICONDUCTOR MODULE

(71) Applicant: Rohm Co., Ltd., Kyoto (JP)

(72) Inventors: Yoshitsugu Uedaira, Kyoto (JP); Koji Saito, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 88 days.

(21) Appl. No.: 14/919,861

(22) Filed: Oct. 22, 2015

(65) Prior Publication Data
US 2016/0113585 A1 Apr. 28, 2016

(30) Foreign Application Priority Data

Oct. 23, 2014 (JP) .................. 2014-216334

(51) Int. Cl.
| | |
|---|---|
| *A61B 5/02* | (2006.01) |
| *A61B 5/024* | (2006.01) |
| *G01J 1/44* | (2006.01) |
| *G01J 1/42* | (2006.01) |
| *A61B 5/00* | (2006.01) |

(52) U.S. Cl.
CPC ........ *A61B 5/02427* (2013.01); *A61B 5/7214* (2013.01); *G01J 1/4228* (2013.01); *G01J 1/44* (2013.01); *A61B 5/7257* (2013.01)

(58) Field of Classification Search
CPC .............. A61B 5/02416; A61B 5/02427
See application file for complete search history.

(56) References Cited

U.S. PATENT DOCUMENTS

| | | | |
|---|---|---|---|
| 2007/0276632 A1* | 11/2007 | Banet ................ | A61B 5/021 702/187 |
| 2012/0150047 A1 | 6/2012 | Terumoto et al. | |
| 2014/0276089 A1* | 9/2014 | Kirenko ............. | A61B 5/01 600/473 |
| 2016/0113529 A1* | 4/2016 | Aoyagi ............. | A61B 5/02108 600/480 |
| 2016/0270708 A1* | 9/2016 | Tateda .............. | A61B 5/029 |

FOREIGN PATENT DOCUMENTS

JP 2012-143316 8/2012

* cited by examiner

Primary Examiner — Eric D. Bertram
(74) Attorney, Agent, or Firm — Fish & Richardson P.C.

(57) ABSTRACT

A pulse wave sensor includes: a white LED emitting white light to a human body; a G sensor converting, into a first electrical signal, green light included in light emitted from the white LED and reflected within the human body; an R sensor converting, into a second electrical signal, red light included in the light emitted from the white LED and reflected within the human body; and an arithmetic control unit configured to generate a signal showing a heart rate based on a level difference between the first electrical signal and the second electrical signal. Therefore, a distance between the G sensor and the R sensor does not have to be increased, so that an apparatus can be reduced in size.

15 Claims, 7 Drawing Sheets

PULSE WAVE SENSOR AND SEMICONDUCTOR MODULE

BACKGROUND OF THE INVENTION

Field of the Invention

The present invention relates to a pulse wave sensor and a semiconductor module, and particularly to a pulse wave sensor and a semiconductor module for detecting information related to a pulse wave in a living body.

Description of the Background Art

Japanese Patent Laying-Open No. 2012-143316 (PTD 1) discloses a pulse wave sensor provided with a first optical sensor, a second optical sensor, and an arithmetic circuit. The first optical sensor includes a first light emitting unit emitting light of the first luminescence intensity to a living body, and a first light receiving unit receiving the light emitted from the first light emitting unit and reflected within the living body to generate a first light receiving signal. The second optical sensor includes a second light emitting unit emitting light of the second luminescence intensity lower than the first luminescence intensity to a living body, and a second light receiving unit receiving the light emitted from the second light emitting unit and reflected within the living body to generate a second light receiving signal. The arithmetic circuit subtracts the second light receiving signal from the first light receiving signal to obtain pulse wave data.

SUMMARY OF THE INVENTION

According to PTD 1, however, the light emitted from the first light emitting unit needs to be prevented from reflecting within the living body and entering the second light receiving unit. Accordingly, it becomes necessary to increase the distance between the first light receiving unit and the second light receiving unit, which causes a problem that the apparatus is increased in size.

Therefore, a main object of the present invention is to provide a pulse wave sensor and a semiconductor module that are reduced in size.

A pulse wave sensor and a semiconductor module according to the present invention include: a light emitting unit configured to emit light including green light and red light to a living body; a first light receiving unit configured to convert, into a first electrical signal, the green light included in light emitted from the light emitting unit and reflected within the living body; a second light receiving unit configured to convert, into a second electrical signal, the red light included in the light emitted from the light emitting unit and reflected within the living body; and an arithmetic control unit configured to detect information related to a pulse wave in the living body based on a level difference between the first electrical signal and the second electrical signal.

In the pulse wave sensor and the semiconductor module according to the present invention, light is emitted from the light emitting unit to a living body, green light included in the reflected light is converted by the first light receiving unit into a first electrical signal, and red light included in the reflected light is converted by the second light receiving unit into a second electrical signal, to detect information related to the pulse wave in the living body based on the level difference between the first electrical signal and the second electrical signal. Accordingly, the distance between the first and second light receiving units does not have to be increased, so that the apparatus can be reduced in size.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

First Embodiment

Figure 1:
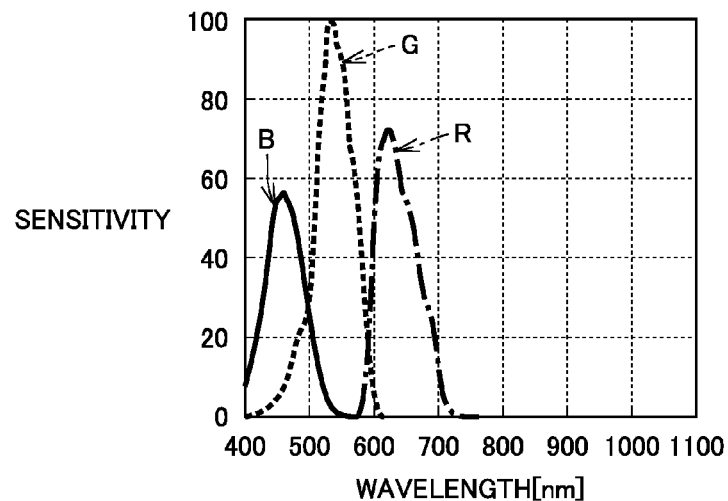
FIG. 1 is a diagram showing the spectral sensitivity of each of an R sensor, a G sensor, and a B sensor.

The principle of the invention of the present application will be first hereinafter described before describing the embodiments. FIG. 1 is a diagram showing the spectral sensitivity of each of an R (red light) sensor, a G (green light) sensor, and a B (blue light) sensor. In FIG. 1, the R sensor has sensitivity to red light having a wavelength λ of about 600 nm to 700 nm, and outputs an electrical signal of a level in accordance with the light intensity of red light included in the incoming white light. The G sensor has sensitivity to green light having a wavelength λ of about 500 nm to 600 nm, and outputs an electrical signal of a level in accordance with the light intensity of green light included in the incoming white light. The B sensor has sensitivity to blue light having a wavelength λ of about 400 nm to 500 nm, and outputs an electrical signal of a level in accordance with the light intensity of blue light included in the incoming white light.

Figure 2:
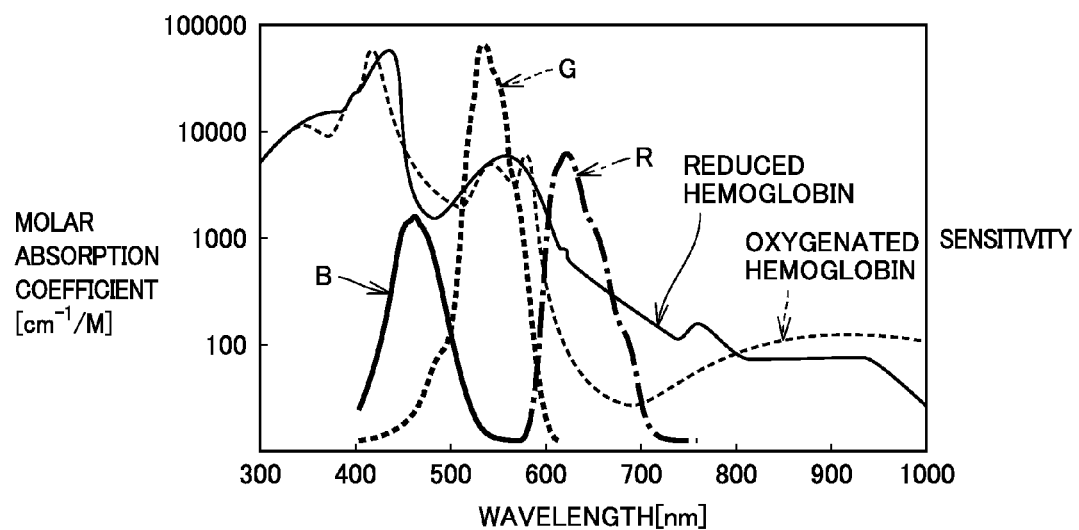
FIG. 2 is a diagram showing the relation among the wavelength of light, the molar absorption coefficient of hemoglobin, and the sensitivity of each of the R sensor, the G sensor and the B sensor.

FIG. 2 is a diagram showing the relation among the wavelength λ [nm] of light, the molar absorption coefficient [$cm^{-1}$/M] of hemoglobin, and the sensitivity of each of the R sensor, the G sensor and the B sensor. In FIG. 2, a thin dotted line shows the molar absorption coefficient of oxygenated hemoglobin while a thin solid line shows the molar absorption coefficient of reduced hemoglobin. Oxygenated hemoglobin is contained in blood in an artery, and reduced hemoglobin is contained in blood in a vein.

In FIG. 2, the molar absorption coefficient of oxygenated hemoglobin to red light having a wavelength λ of 650 nm is approximately 50 $cm^{-1}$/M, whereas the molar absorption coefficient of oxygenated hemoglobin to green light having a wavelength λ of 550 nm is approximately 5000 $cm^{-1}$/M. Therefore, the molar absorption coefficient of oxygenated hemoglobin to green light is about 100 times greater than the molar absorption coefficient of oxygenated hemoglobin to red light.

A pulse wave in a human body shows changes in the blood flow in an artery, and the molar absorption coefficient of oxygenated hemoglobin changes in accordance with such changes. Accordingly, if white light is emitted to a human body, and the light intensity of green light included in the light reflected within the human body is detected by the G sensor, a pulse wave in a human body can be detected. On the other hand, even if white light is emitted to a human body, and the light intensity of red light included in the light reflected within the human body is detected by the R sensor, a pulse wave in a human body can hardly be detected. If a G sensor is used, a pulse wave can be detected with the sensitivity that is about 100 times higher than that in the case where an R sensor is used. In this case, however, the body motion produces a noise when detecting a pulse wave in a human body.

Figure 3:
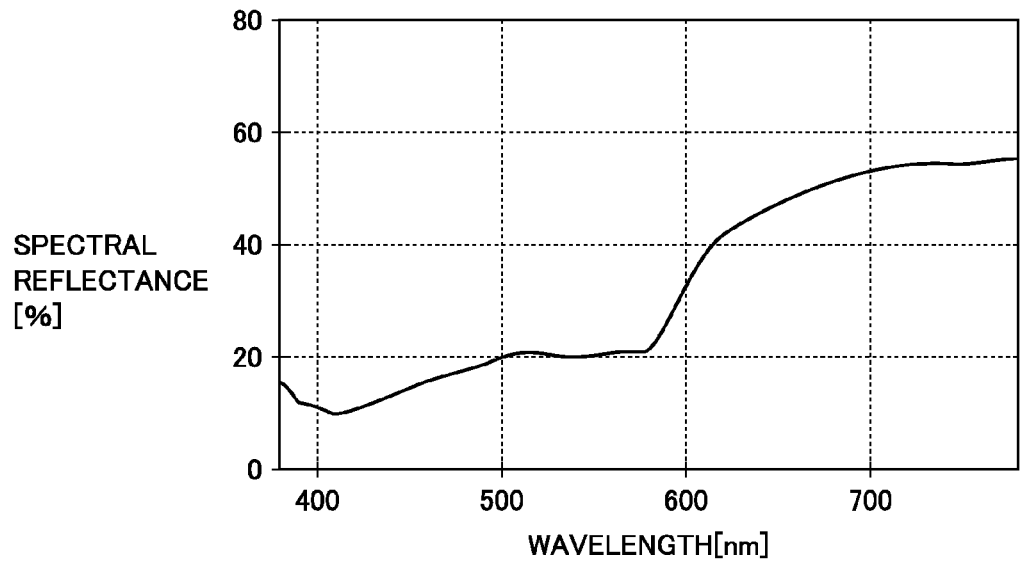
FIG. 3 is a diagram showing the spectral reflectance of human skin.

FIG. 3 is a diagram showing the spectral reflectance [%] of human skin. In FIG. 3, the spectral reflectance of human skin to red light having a wavelength λ of 650 nm is about 45%, whereas the spectral reflectance of human skin to green light having a wavelength λ of 550 nm is about 20%. Accordingly, the spectral reflectance of human skin to green light is about one half of the spectral reflectance of human skin to red light.

The spectral reflectance of human skin changes in accordance with the human body motion. Accordingly, if white light is emitted to a human body and the light intensity of green light included in the light reflected within the human body is detected by a G sensor, human body motion can be detected. Furthermore, also if white light is emitted to a human body and the light intensity of red light included in the light reflected within the human body is detected by an R sensor, human body motion can be detected. If a G sensor is used, body motion can be detected with the sensitivity that is about one half of the sensitivity in the case where an R sensor is used. Accordingly, in the invention of the present application, a pulse wave and body motion are detected using a G sensor while body motion is detected using an R sensor. Then, based on the detection results of the G sensor and the R sensor, a pulse wave is detected.

In other words, according to the invention of the present application, white light is emitted to a human body, and then, the light intensity of green light included in the light reflected within the human body is detected by a G sensor while the light intensity of red light included in the light reflected within the human body is detected by an R sensor. The output signal from the G sensor includes: a pulse wave component that changes in accordance with the pulse wave in a human body; and a body motion component that changes in accordance with the human body motion. The output signal from the R sensor includes a body motion component. At least one of output signals from the G sensor and the R sensor is amplified or attenuated such that the level of the body motion component of the output signal from the G sensor and the level of the body motion component of the output signal from the R sensor are identical to each other. After that, one of the output signals from the G sensor and the R sensor is subtracted from the other output signal to thereby extract a pulse wave component of the output signal from the G sensor. The information related to the pulse wave in a human body (for example, a heart rate) is obtained based on the extracted pulse wave component. The invention of the present application will be hereinafter described in detail with reference to the accompanying drawings.

Figure 4:
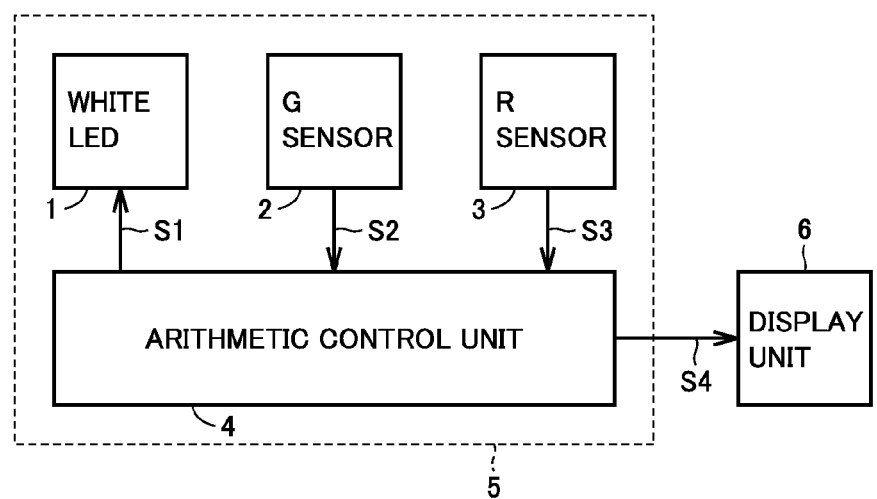
FIG. 4 is a block diagram showing the configuration of a pulse wave sensor according to the first embodiment of the present invention.

FIG. 4 is a block diagram showing the configuration of a pulse wave sensor according to the first embodiment of the present invention. In FIG. 4, the pulse wave sensor includes: a sensor main body 5 (a semiconductor module) having a white LED (Light Emitting Diode) 1, a G sensor 2, an R sensor 3, and an arithmetic control unit 4; and a display unit 6. Sensor main body 5 is modularized and attached to a human body (not shown), for example, a finger, a wrist, an ear, and the like. Display unit 6 is attached to clothes and the like of a human test subject. Sensor main body 5 and display unit 6 are connected to each other by an electric wire or the like. Sensor main body 5 and display unit 6 may be integrally formed.

White LED 1 emits light in response to a control signal S1 from arithmetic control unit 4 and emits white light to a human body. The white light emitted from white LED 1 is reflected within the human body and enters G sensor 2 and R sensor 3. At this time, the white light is absorbed into skin, blood and the like, and the intensity of the reflected light changes in accordance with the pulse wave and the body motion of the human body. Examples of body motion may be muscular contraction or the like caused, for example, by jogging, walking, and the like.

G sensor 2 converts, into an electrical signal S2, green light included in the incoming light that has been emitted from white LED 1 and reflected within the human body. The level (for example, a voltage) of electrical signal S2 rises in accordance with the light intensity of the incoming green light. As described above, the level of electrical signal S2 changes in accordance with the pulsation and body motion in a human body.

R sensor 3 converts, into an electrical signal S3, red light included in the incoming light that has been emitted from white LED 1 and reflected within the human body. The level (for example, a voltage) of electrical signal S3 rises in accordance with the light intensity of the incoming red light. As described above, electrical signal S3 changes in accordance with the human body motion, but hardly changes in accordance with the pulsation in a human body.

Arithmetic control unit 4 amplifies at least one electrical signal (for example, S3) of electrical signals S2 and S3 such that the amplitudes of the body motion components of electrical signals S2 and S3 that change in the same period are approximately the same. Arithmetic control unit 4 calculates an electrical signal S23 that shows the level difference between electrical signal S2 and an electrical signal S3A obtained by amplifying electrical signal S3, and then, obtains a pulse wave in a human body based on this electrical signal S23.

Figure 5:
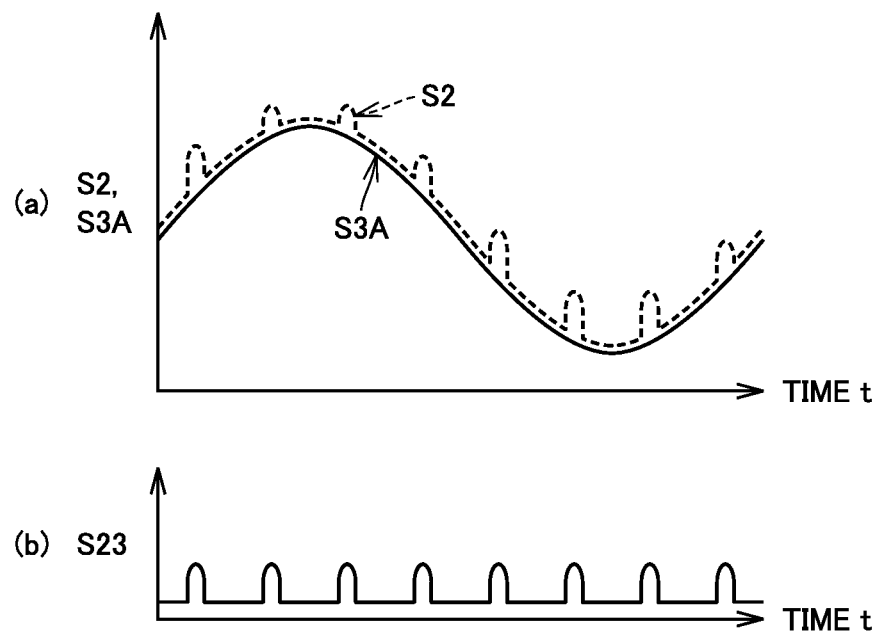
FIG. 5 is a time chart illustrating the operation of the pulse wave sensor shown in FIG. 4.

FIGS. 5(a) and 5(b) each are a time chart illustrating the operation of the pulse wave sensor shown in FIG. 4. FIG. 5(a) illustrates waveforms of electrical signals S2 and S3A while FIG. 5(b) illustrates a waveform of electrical signal S23. In FIGS. 5(a) and 5(b), electrical signal S2 includes a body motion component that changes in a relatively long period and in a relatively large amplitude, and a pulse wave component that changes in a relatively short period and in a relatively small amplitude, and also, electrical signal S3A includes a body motion component that is approximately the same as that of electrical signal S2. Electrical signal S23 showing the level difference between electrical signal S2 and electrical signal S3A includes only a pulse wave component.

Electrical signal S23 includes information related to a pulse wave in a human body. The pulse wave that is under control of a heart and autonomic nerves does not always show a fixed behavior, but shows various changes (fluctuations) depending on the test subject's state. Accordingly, such changes (fluctuations) in the pulse wave are analyzed, so that various pieces of information about the test subject's body can be obtained. Examples of information related to a pulse wave include a heart rate, heart rate variability, an acceleration plethysmogram, and the like.

A heart rate shows the number of pulses per minute. Based on the heart rate, it becomes possible to obtain information about the test subject's athletic ability, tension level, and the like. The heart rate variability shows the temporal change in the heart rate. Based on the heart rate variability, it becomes possible to obtain information about the test subject's fatigue degree, good sleep level, stress level, and the like. The acceleration plethysmogram is obtained by differentiating a pulse wave twice along the time axis. Based on the acceleration plethysmogram, it becomes possible to obtain information about the test subject's vascular age, arteriosclerosis degree, and the like.

Arithmetic control unit 4 calculates, for example, a heart rate based on electrical signal S23, and outputs a signal S4 showing the calculated heart rate to display unit 6. According to signal S4 from arithmetic control unit 4, display unit 6 displays a character, an image and the like showing the heart rate on its screen.

Figure 6:
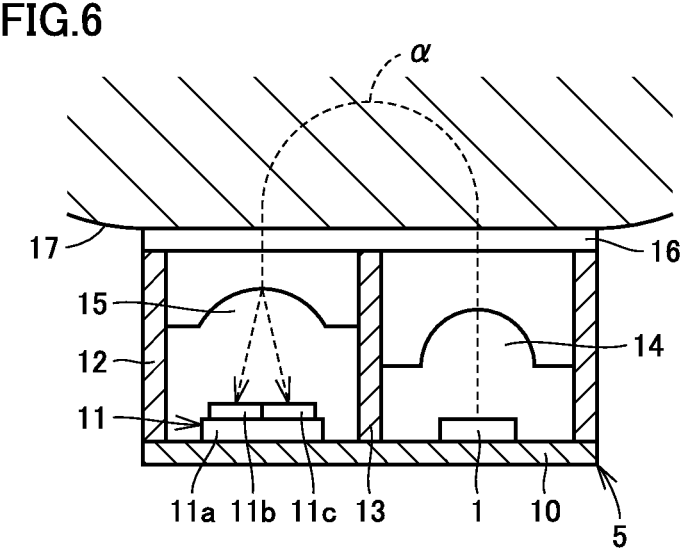
FIG. 6 is a cross-sectional view showing the configuration of a sensor main body shown in FIG. 4.

FIG. 6 is a cross-sectional view showing the configuration of sensor main body 5. In FIG. 6, sensor main body 5 is modularized and includes: a substrate 10; and a white LED 1 and a light receiving IC (Integrated Circuit) 11 that are mounted on the surface of substrate 10. Light receiving IC 11 includes a substrate 11a, and a G filter 11b and an R filter 11c that are formed on the surface of substrate 11a. G filter 11b allows only green light included in the incoming white light to pass therethrough. R filter 11c allows only red light included in the incoming white light to pass therethrough.

On the surface of substrate 11a, a first photoelectric conversion circuit and a second photoelectric conversion circuit are mounted. The first photoelectric conversion circuit serves to convert the green light having passed through G filter 11b into electrical signal S2. The second photoelectric conversion circuit serves to convert the red light having passed through R filter 11c into electrical signal S3. G filter 11b and the first photoelectric conversion circuit constitute G sensor 2. R filter 11c and the second photoelectric conversion circuit constitute R sensor 3. Arithmetic control unit 4 is formed on the surface of substrate 10a or 10, and generates an electrical signal S4 based on electrical signals S2 and S3.

An annular light shielding wall 12 is formed on the edge of the surface of substrate 10 so as to surround white LED 1 and light receiving IC 10. Light shielding wall 12 serves to prevent external light from entering light receiving IC 11. A light shielding wall 13 is formed at the center on the surface of substrate 10. Light shielding wall 13 serves to prevent white light, which has been emitted from white LED 1, from directly entering light receiving IC 10. In other words, a rectangular parallelepiped space provided by light shielding wall 12 is partitioned by light shielding wall 13 into two spaces.

Two spaces surrounded by light shielding walls 12 and 13 include: one space in which a lens 14 is provided on white LED 1; and the other space in which a lens 15 is provided on light receiving IC 11. The openings at the upper ends of light shielding walls 12 and 13 are closed by a transparent plate 16. When a pulse wave is detected, the surface of transparent plate 16 is brought into contact with the surface of a human body 17.

White light $\alpha$ emitted from white LED 1 is applied through lens 14 and transparent plate 16 to human body 17, reflected while passing through the human body, and enters light receiving IC 11 through transparent plate 16 and lens 15. Green light included in white light $\alpha$ having entered light receiving IC 11 passes through G filter 11b and enters substrate 11. Then, the incoming green light is converted into electrical signal S2 by the first photoelectric conversion circuit. Furthermore, red light included in white light $\alpha$ having entered light receiving IC 11 passes through R filter 11c and enters substrate 11. Then, the incoming red light is converted into electrical signal S3 by the second photoelectric conversion circuit. Arithmetic control unit 4 generates electrical signal S4 based on electrical signals S2 and S3.

Figure 7:
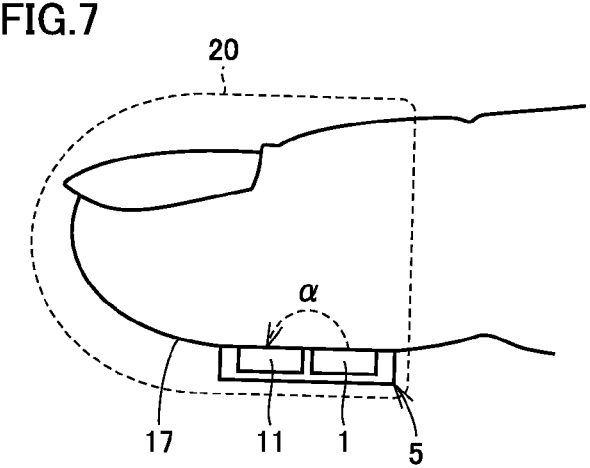
FIG. 7 is a diagram showing how to attach the sensor main body shown in FIG. 6 to a human body.

FIG. 7 is a diagram showing how to attach sensor main body 5 shown in FIG. 6 to human body 17. In FIG. 7, a pulse wave sensor includes a finger sack-type housing 20. Sensor main body 5 is provided inside housing 20 such that white LED 1 and light receiving IC 11 face a pad of a finger (a palm of a hand) when finger sack-type housing 20 is attached to the finger tip of human body 17. In this way, white LED 1 and light receiving IC 11 are arranged on the thick and good-fitting pad of the finger (on the palm of the hand), thereby allowing a pulse wave to be stably measured, so that the pulse wave measurement accuracy can be improved. Furthermore, finger sack-type housing 20 also functions as a light shielding member that covers sensor main body 5. By providing the configuration as described above, a pulse wave can be stably measured without being influenced by light from the outside.

As described above, in the present first embodiment, white light $\alpha$ is emitted from white LED 1 to human body 17. Green light included in the reflected light is converted into first electrical signal S2 by G sensor 2 while red light included in the reflected light is converted into second electrical signal S3 by R sensor 3. Then, a pulse wave is detected based on the level difference between first electrical signal S2 and second electrical signal S3. Therefore, since the distance between G sensor 2 and R sensor 3 does not have to be increased, the apparatus can be increased in size.

In addition, white LED 1 emitting white light $\alpha$ is used in the present first embodiment. However, since only green light and red light included in white light $\alpha$ are used, a green LED that emits green light and a red LED that emits red light may be provided in place of white LED 1.

Furthermore, although one white LED 1 and one light receiving IC 11 are used, a plurality of white LEDs 1 and one light receiving IC 11 may be used in such a configuration in which one light receiving IC 11 is arranged in the center of the plurality of white LEDs 1. Also, it goes without saying that not only a pulse wave in a human body but also a pulse wave in a living body including humans and animals can be detected.

Figure 8:
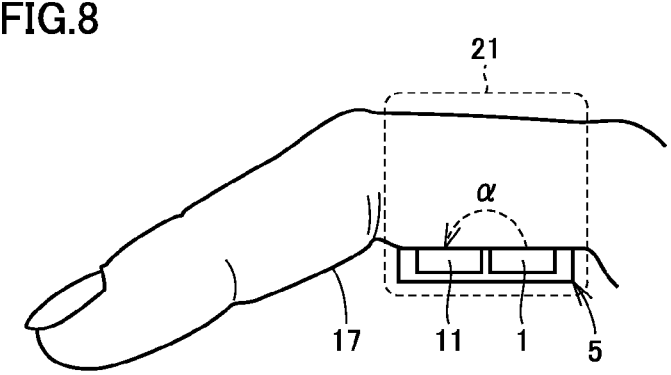
FIG. 8 is a diagram showing a modification of the first embodiment.

FIG. 8 is a diagram showing a modification of the first embodiment, which is compared with FIG. 7. This pulse wave sensor is different from the pulse wave sensor in FIG. 7 in that finger sack-type housing 20 is replaced with a finger ring-type housing 21. Sensor main body 5 is provided inside housing 21 such that white LED 1 and light receiving IC 11 face the pad of the finger (the palm of the hand) when finger ring-type housing 21 is attached to the finger of human body 17 between the second joint and the third joint. In this way, white LED 1 and light receiving IC 11 are arranged on the thick and good-fitting pad of the finger (on the palm of the hand), thereby allowing a pulse wave to be stably measured, so that the pulse wave measurement accuracy can be improved. Furthermore, since finger ring-type housing 21 also functions as a light shielding member that covers sensor main body 5, a pulse wave can be stably measured without being influenced by the light from the outside. Furthermore, since finger ring-type housing 21 is used, sensor main body 5 can be prevented from slipping off the finger.

Figure 9:
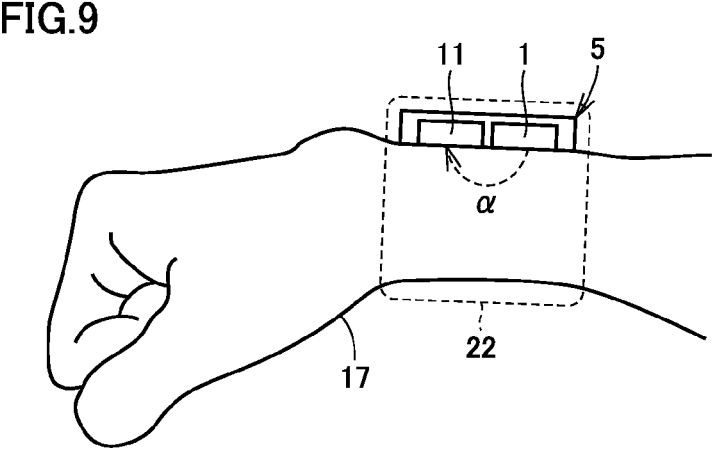
FIG. 9 is a diagram showing another modification of the first embodiment.

FIG. 9 is a diagram showing another modification of the first embodiment, which is compared with FIG. 7. This pulse wave sensor is different from the pulse wave sensor in FIG. 7 in that finger sack-type housing 20 is replaced with a bracelet-type housing 22. Sensor main body 5 is provided inside housing 20 such that white LED 1 and light receiving IC 11 are located in the center portion on the back of the wrist (on the back of the hand) when bracelet-type housing 22 is attached to the wrist of human body 17. In this way, white LED 1 and light receiving IC 11 are arranged in the center portion on the thick and good-fitting back of the wrist (on the back of the hand), thereby allowing a pulse wave to be stably measured, so that the pulse wave measurement accuracy can be improved. Furthermore, since bracelet-type housing 22 functions also as a light shielding member that covers sensor main body 5, a pulse wave can be stably measured without being influenced by the light from the outside. Furthermore, since bracelet-type housing 22 is used, sensor main body 5 can be prevented from slipping off an arm.

Second Embodiment

Figure 10:
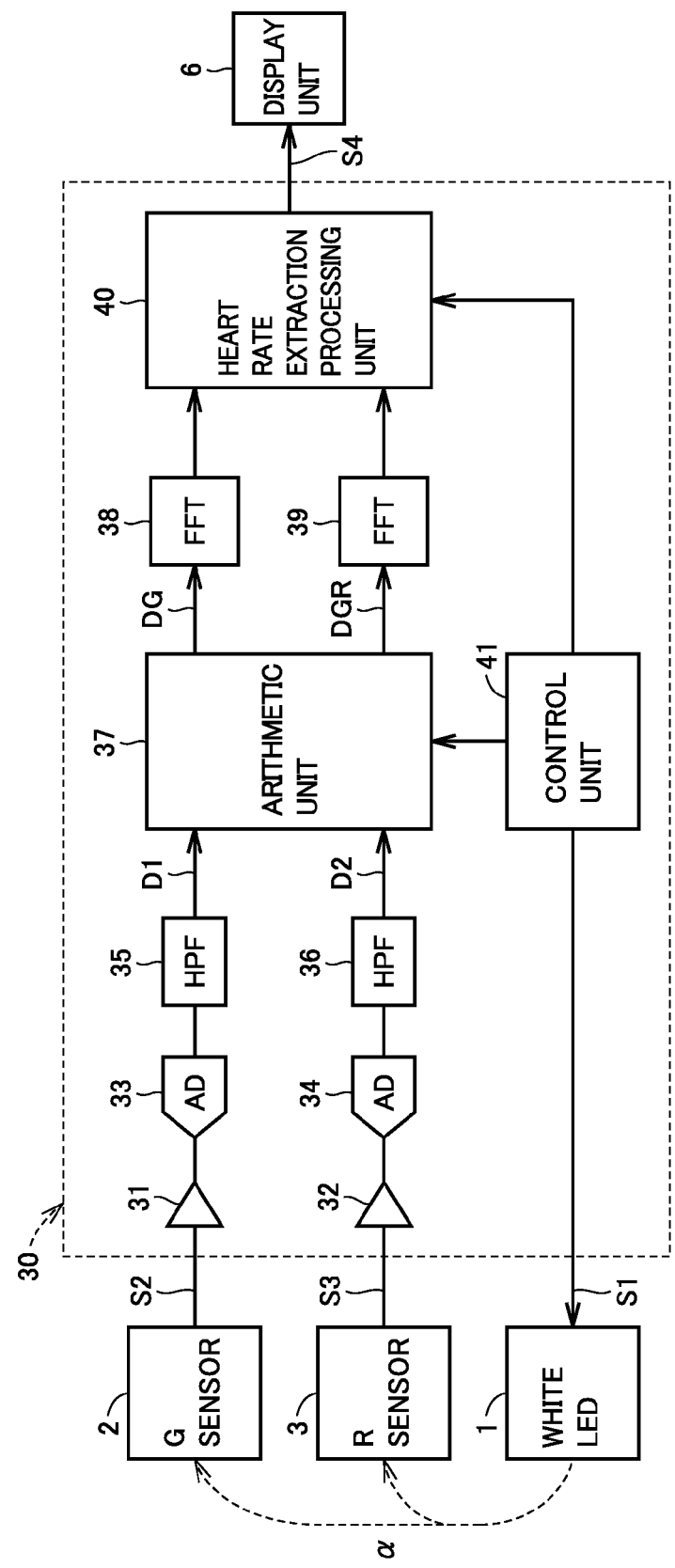
FIG. 10 is a block diagram showing the configuration of a pulse wave sensor according to the second embodiment of the present invention.

FIG. 10 is a block diagram showing the configuration of a pulse wave sensor according to the second embodiment of the present invention, which is compared with FIG. 4. Referring to FIG. 10, this pulse wave sensor is different from the pulse wave sensor in FIG. 4 in that arithmetic control unit 4 is replaced with an arithmetic control unit 30.

Arithmetic control unit 30 includes amplifiers 31 and 32, AD (analog-to-digital) converters 33 and 34, high-pass filters (HPF) 35 and 36, an arithmetic unit 37, FFT (Fast Fourier Transform) units 38 and 39, a heart rate extraction processing unit 40, and a control unit 41.

Control unit 41 turns control signal S1 alternately into an "H" level and an "L" level at the frequency that is sufficiently higher than the frequency of the pulse wave, to thereby turn on and off white LED 1. Also, control unit 41 controls entire arithmetic control unit 30 in synchronization with control signal S1.

G sensor 2 receives white light emitted from white LED 1 and reflected within the human body, and the light leaked thereinto from the outside in accordance with the body motion. Then, G sensor 2 outputs electrical signal S2 of the level in accordance with the light intensity of the green light included in the received light. R sensor 3 receives white light emitted from white LED 1 and reflected within the human body, and the light leaked thereinto from the outside in accordance with the body motion. Then, R sensor 3 outputs electrical signal S3 of the level in accordance with the light intensity of the red light included in the received light.

Amplifier 31 amplifies electrical signal S2 output from G sensor 2. AD converter 33 converts the output signal from amplifier 31 into a digital signal. High-pass filter 35 removes a direct-current (DC) component in the output signal of AD converter 33. The signal having passed through high-pass filter 35 is supplied to arithmetic unit 37 as a digital signal D1.

Amplifier 32 amplifies electrical signal S3 output from R sensor 3. AD converter 34 converts the output signal from amplifier 32 into a digital signal. High-pass filter 36 removes a DC component in the output signal of AD converter 34. The signal having passed through high-pass filter 36 is supplied to arithmetic unit 37 as a digital signal D2.

Figure 11:
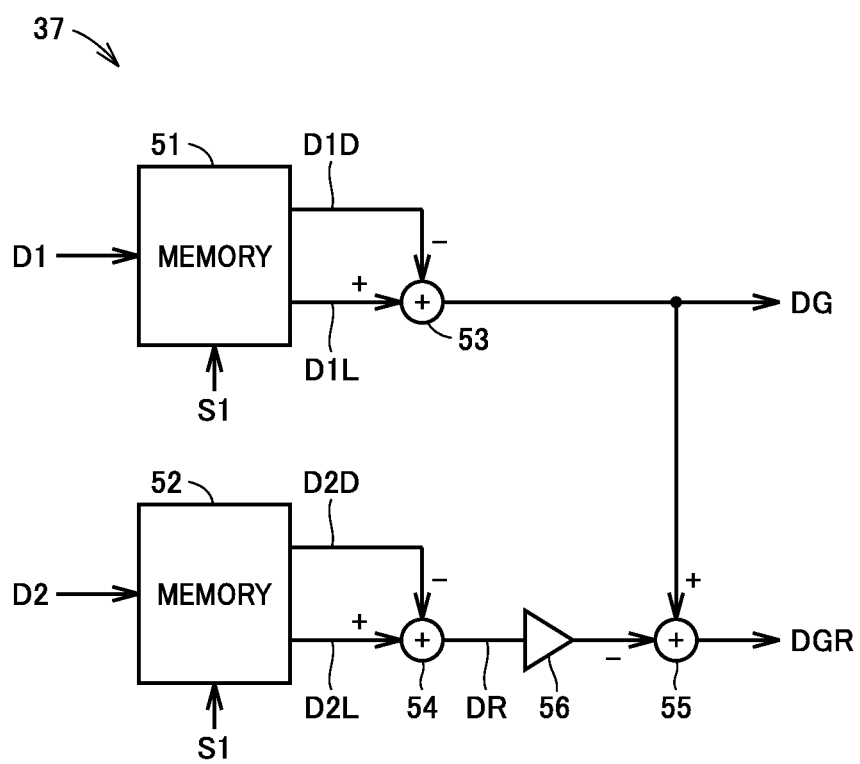
FIG. 11 is a block diagram showing the configuration of an arithmetic unit shown in FIG. 10.

Arithmetic control unit 37 includes memories 51 and 52, subtracters 53 to 55, and an amplifier 56, as shown in FIG. 11. Memory 51 temporarily stores digital signal D1 as a digital signal D1D in a time period during which control signal S1 is at an "L" level (that is, the time period during which white LED 1 is turned off), and temporarily stores digital signal D1 as a digital signal D1L in a time period during which control signal S1 is at an "H" level (that is, the time period during which white LED 1 is turned on). After that, memory 51 outputs digital signals D1D and D1L to subtracter 53 at the same time.

Digital signal D1D includes a noise component resulting from the light and the like having leaked into G sensor 2 from the outside in the time period during which white LED 1 is turned off. This noise component is included also in digital signal D1L. Subtracter 53 subtracts digital signal D1D from digital signal D1L, and outputs a digital signal DG. Therefore, digital signal DG is a signal obtained by removing a noise component from digital signal D1L.

Similarly, memory 52 temporarily stores digital signal D2 as a digital signal D2D in a time period during which control signal S1 is at an "L" level (that is, the time period during which white LED 1 is turned off), and also temporarily stores digital signal D2 as a digital signal D2L in a time period during which control signal S1 is at an "H" level (that is, the time period during which white LED 1 is turned on). After that, memory 52 outputs digital signals D2D and D2L to subtracter 54 at the same time.

Digital signal D2D includes a noise component resulting from the light and the like having leaked into R sensor 3 from the outside in the time period during which white LED 1 is turned off. This noise component is included also in digital signal D2L. Subtracter 56 subtracts digital signal D2D from digital signal D2L, and outputs digital signal DR. Therefore, digital signal DR is a signal obtained by removing a noise component from digital signal D2L.

Digital signal DG includes a body motion component and a pulse wave component. Digital signal DR includes a body motion component. Amplifier 56 amplifies digital signal DR such that the level of the body motion component included in digital signal DG and the level of the body motion component included in digital signal DR are almost the same. Subtracter 55 subtracts the output digital signal of amplifier 56 from output digital signal DG of subtracter 53, and outputs a digital signal DGR.

In addition, although digital signal DR is amplified by amplifier 56 in arithmetic control circuit 37 shown in FIG. 11, the present invention is not limited thereto, but at least one of digital signals DG and DR may be amplified or attenuated such that the levels of the body motion components included in digital signals DG and DR are almost the same.

Referring back to FIG. 10, FFT unit 38 applies fast Fourier transform to digital signal DG to generate a frequency spectrum diagram of digital signal DG, and supplies the generated frequency spectrum diagram to heart rate extraction processing unit 40. FFT unit 39 applies fast Fourier transform to digital signal DGR to generate a frequency spectrum diagram of digital signal DGR, and supplies the generated frequency spectrum diagram to heart rate extraction processing unit 40. Heart rate extraction processing unit 40 calculates the heart rate of a human body based on the frequency spectrum diagrams supplied from FFT units 38 and 39, and outputs a signal S4 showing the calculated heart rate to display unit 6.

Figure 12:
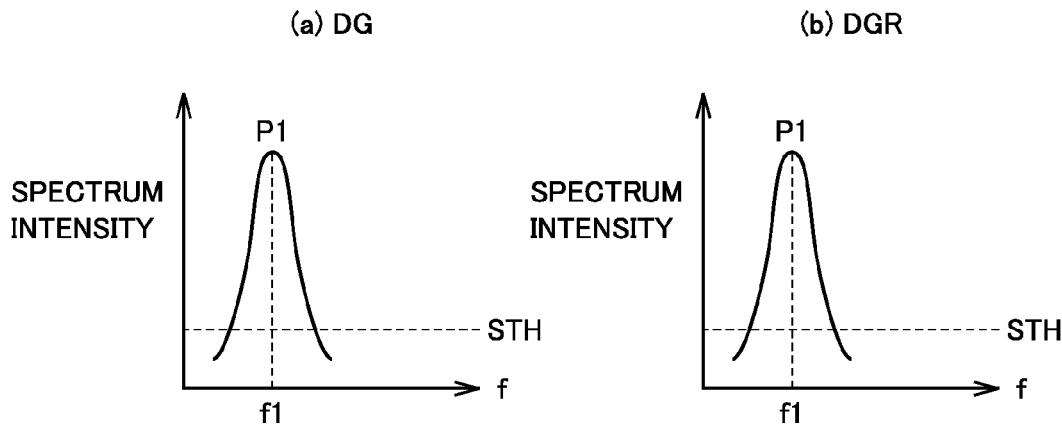
FIG. 12 is a frequency spectrum diagram showing the operation of a heart rate extraction processing unit shown in FIG. 10.
Figure 13:
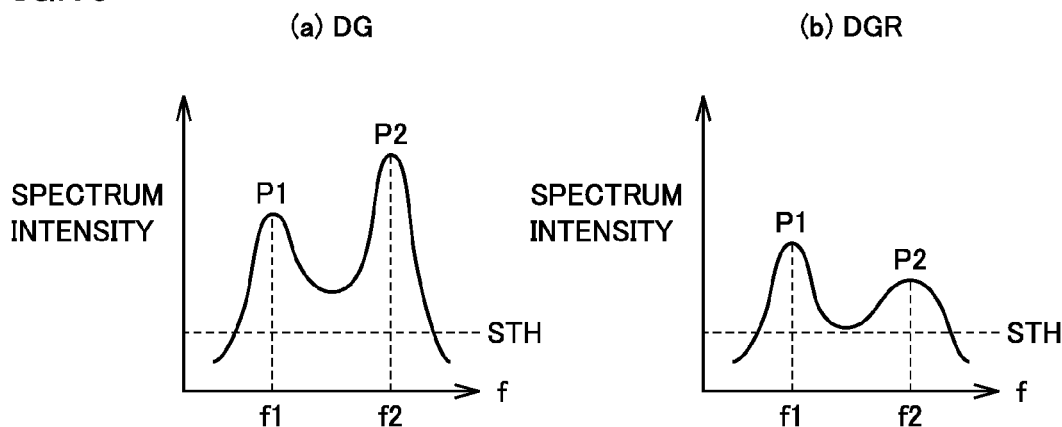
FIG. 13 is another frequency spectrum diagram showing the operation of the heart rate extraction processing unit shown in FIG. 10.
Figure 14:
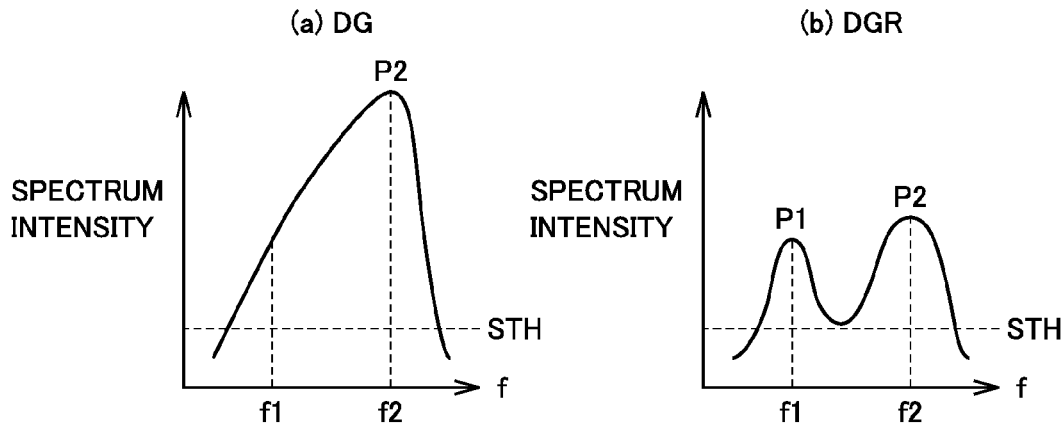
FIG. 14 is still another frequency spectrum diagram showing the operation of the heart rate extraction processing unit shown in FIG. 10.

The operation of heart rate extraction processing unit 40 will be hereinafter described. FIGS. 12(a), 13(a) and 14(a) each are a frequency spectrum diagram of digital signal DG generated in FFT unit 38. FIGS. 12(b), 13(b) and 14(b) each are a frequency spectrum diagram of digital signal DGR generated in FFT unit 39. The frequency of the peak at which the spectrum intensity falls within a range equal to or greater than a predetermined threshold value STH is defined as a candidate of the frequency of a pulse wave.

When the human body motion is relatively small (for example, when the test subject remains stationary), the frequency spectra of digital signals DG and DGR each show a crest-shaped curved line including one peak P1, as shown in FIGS. 12(a) and 12(b). In this case, heart rate extraction processing unit 40 determines a frequency f1 of peak P1 as a frequency of the pulse wave, calculates the heart rate [times/minute] based on this frequency f1, and outputs signal S4 showing this heart rate [times/minute]. In the case where the body motion is relatively small in this way, heart rate extraction processing unit 40 calculates the heart rate [times/minute] in a relatively short period T1, and outputs signal S4 showing the heart rate [times/minute].

When the human body motion is relatively large (for example, when the test subject is jogging), the frequency spectra of digital signals DG and DGR each show a crest-shaped curved line including two peaks P1 and P2, as shown in FIGS. 13(a) and 13(b). In this case, heart rate extraction processing unit 40 calculates the rate at which the heights of peaks P1 and P2 of the frequency spectrum of digital signal DGR decreases with respect to the heights of peaks P1 and P2 of the frequency spectrum of digital signal DG (the decrease rate). Then, heart rate extraction processing unit 40 determines frequency f1 of the peak with the lower decrease rate (in this case, P1) as a frequency of the pulse wave, calculates the heart rate [times/minute] based on this frequency f1, and outputs signal S4 showing the heart rate [times/minute]. In the case where the body motion is relatively large in this way, heart rate extraction processing unit 40 calculates the heart rate [times/minute] in a relatively long period T2, and outputs signal S4 showing the heart rate [times/minute]. In this case, T2>T1.

In the case where the human body motion is relatively large (for example, when the test subject is jogging), the frequency spectrum of digital signal DG may be a crest-shaped curved line having one peak P2 while the frequency spectrum of digital signal DGR may be a crest-shaped curved line having two peaks P1 and P2, as shown in FIGS. 14(a) and 14(b). In this case, heart rate extraction processing unit 40 determines that frequency f1 of peak P1, which newly appeared due to a decrease in height of peak P2 in the frequency spectrum of digital signal DGR, is the frequency of a pulse wave. Then, heart rate extraction processing unit 40 calculates the heart rate [times/minute] based on this frequency f1, and outputs signal S4 showing this heart rate [times/minute].

In the present second embodiment, white LED 1 is turned on and off in a predetermined period. Also, based on output signals S2 and S3 from sensors 2 and 3, respectively, obtained at the time when white LED 1 is turned off, a noise component is removed from each of output signals S2 and S3 of sensors 2 and 3, respectively, obtained at the time when white LED 1 is turned on. Therefore, a pulse wave can be detected with accuracy.

Furthermore, since the heart rate is calculated based on the frequency spectrum diagrams of digital signals DG and DGR, the heart rate can readily be calculated.

Furthermore, the heart rate is calculated in a relatively short period T1 when the body motion is relatively small. The heart rate is calculated in a relatively long period T2 when the body motion is relatively large. Accordingly, the heart rate during rest can be calculated immediately.

In addition, in the present second embodiment, fast Fourier transform is applied to digital signals DG and DGR to generate frequency spectrum diagrams of digital signals DG and DGR. However, a frequency analysis method different from fast Fourier transform may be employed. For example, discrete Fourier transform may be applied to digital signals DG and DGR to generate frequency spectrum diagrams of digital signals DG and DGR. Also, frequency spectrum diagrams of digital signals DG and DGR may be generated using the maximum entropy method.

Although the embodiments of the present invention have been described as above, it should be understood that the embodiments disclosed herein are illustrative and non-restrictive in every respect. The scope of the present invention is defined by the terms of the claims, and is intended to include any modifications within the meaning and scope equivalent to the terms of the claims.

What is claimed is:
1. A pulse wave sensor comprising:
   a light emitting unit configured to emit light including green light and red light to a living body;
   a first light receiving unit configured to convert, into a first electrical signal, the green light included in light emitted from said light emitting unit and reflected within said living body;
   a second light receiving unit configured to convert, into a second electrical signal, the red light included in the light emitted from said light emitting unit and reflected within said living body; and
   an arithmetic control unit configured to detect information related to a pulse wave in said living body based on a level difference between said first electrical signal and said second electrical signal,
   said arithmetic control unit including:
      a subtracter configured to generate a third electrical signal showing the level difference between said first electrical signal and said second electrical signal,
      a first frequency component analysis unit configured to obtain a frequency spectrum of said first electrical signal, and
      a second frequency component analysis unit configured to obtain a frequency spectrum of said third electrical signal, and
      wherein the arithmetic control unit is configured to compare the frequency spectrum of said first electrical signal and the frequency spectrum of said third electrical signal to obtain the information related to the pulse wave in said living body based on a comparison result.

2. The pulse wave sensor according to claim 1, wherein
said first electrical signal includes a pulse wave component that changes in accordance with the pulse wave in said living body, and a body motion component that changes in accordance with a body motion of said living body, and
said second electrical signal includes said body motion component.

3. The pulse wave sensor according to claim 2, wherein said arithmetic control unit amplifies or attenuates at least one of said first electrical signal and said second electrical signal such that a level of said body motion component of said first electrical signal and a level of said body motion component of said second electrical signal are identical to each other, and then, obtains the level difference to generate said third electrical signal.

4. The pulse wave sensor according to claim 1, wherein
said first frequency component analysis unit applies fast Fourier transform to said first electrical signal to obtain the frequency spectrum of said first electrical signal, and
said second frequency component analysis unit applies fast Fourier transform to said third electrical signal to obtain the frequency spectrum of said third electrical signal.

5. The pulse wave sensor according to claim 1, wherein
said first frequency component analysis unit applies discrete Fourier transform to said first electrical signal to obtain the frequency spectrum of said first electrical signal, and
said second frequency component analysis unit applies discrete Fourier transform to said third electrical signal to obtain the frequency spectrum of said third electrical signal.

6. The pulse wave sensor according to claim 1, wherein
said first frequency component analysis unit obtains the frequency spectrum of said first electrical signal using a maximum entropy method, and
said second frequency component analysis unit obtains the frequency spectrum of said third electrical signal using the maximum entropy method.

7. The pulse wave sensor according to claim 1, wherein
said first electrical signal includes a first noise component resulting from light having leaked into said first light receiving unit from outside,
said second electrical signal includes a second noise component resulting from light having leaked into said second light receiving unit from outside, and
said arithmetic control unit is configured to
turn on and off said light emitting unit in a predetermined period,
based on a signal output from said first light receiving unit at a time when said light emitting unit is turned off, remove said first noise component from said first electrical signal output from said first light receiving unit at a time when said light emitting unit is turned on,
based on a signal output from said second light receiving unit at a time when said light emitting unit is turned off, remove said second noise component from said second electrical signal output from said second light receiving unit at a time when said light emitting unit is turned on, and
detect the information related to the pulse wave in said living body based on the level difference between said first electrical signal and said second electrical signal obtained after said first noise component and said second noise component are removed.

8. The pulse wave sensor according to claim 1, wherein said arithmetic control unit obtains the information related to the pulse wave in said living body in a first period in a case where a level of a body motion of said living body is smaller than a predetermined threshold value, and obtains the information related to the pulse wave in said living body in a second period longer than said first period in a case where the level of the body motion of said living body is larger than said predetermined threshold value.

9. The pulse wave sensor according to claim 1, wherein said light emitting unit is a light emitting diode emitting white light.

10. The pulse wave sensor according to claim 1, further comprising a substrate on which said light emitting unit, said first light receiving unit, said second light receiving unit, and said arithmetic control unit are mounted.

11. The pulse wave sensor according to claim 1, further comprising a light shielding member configured to prevent external light from entering said first light receiving unit and said second light receiving unit.

12. The pulse wave sensor according to claim 1, wherein the information related to the pulse wave in said living body is a heart rate of said living body.

13. A semiconductor module comprising the pulse wave sensor according to claim 1.

14. A pulse wave sensor operable to receive light emitted from a light emitting unit to a living body and reflected within the living body, the light emitting unit operable to emit light including green light and red light, the pulse wave sensor comprising:
a first light receiving unit configured to convert, into a first electrical signal, the green light included in light emitted from said light emitting unit and reflected within said living body;
a second light receiving unit configured to convert, into a second electrical signal, the red light included in the light emitted from said light emitting unit and reflected within said living body; and
an arithmetic control unit configured to detect information related to a pulse wave in said living body based on a level difference between said first electrical signal and said second electrical signal,
said arithmetic control unit including:
a subtracter configured to generate a third electrical signal showing the level difference between said first electrical signal and said second electrical signal,
a first frequency component analysis unit configured to obtain a frequency spectrum of said first electrical signal, and
a second frequency component analysis unit configured to obtain a frequency spectrum of said third electrical signal, and
wherein the arithmetic control unit is configured to compare the frequency spectrum of said first electrical signal and the frequency spectrum of said third electrical signal to obtain the information related to the pulse wave in said living body based on a comparison result.

15. A pulse wave sensor comprising:
a light emitting unit configured to emit light including green light and red light to a living body;

a first light receiving unit configured to convert, into a first electrical signal, the green light included in light emitted from said light emitting unit and reflected within said living body;

a second light receiving unit configured to convert, into a second electrical signal, the red light included in the light emitted from said light emitting unit and reflected within said living body; and an arithmetic control unit configured to detect information related to a pulse wave in said living body based on a level difference between said first electrical signal and said second electrical signal, wherein said first electrical signal includes a pulse wave component that changes in accordance with the pulse wave in said living body, and a body motion component that changes in accordance with a body motion of said living body, said second electrical signal includes said body motion component, and said arithmetic control unit is configured to remove said body motion component from said first electrical signal based on said second electrical signal to generate a third electrical signal including said pulse wave component, and to detect the information related to the pulse wave in said living body based on said third electrical signal.

* * * * *